(12) United States Patent
Ju et al.

(10) Patent No.: US 11,712,279 B2
(45) Date of Patent: Aug. 1, 2023

(54) ORTHOPEDIC IMPACTOR

(71) Applicant: IMEDICOM CO., LTD., Gunpo-si (KR)

(72) Inventors: Don Soo Ju, Gunpo-si (KR); Byoung Ju Lee, Gunpo-si (KR); Jin Tae Sang, Gunpo-si (KR)

(73) Assignee: IMEDICOM CO., LTD., Gunpo-si (KR)

( * ) Notice: Subject to any disclaimer, the term of this patent is extended or adjusted under 35 U.S.C. 154(b) by 0 days.

(21) Appl. No.: 18/008,022

(22) PCT Filed: Mar. 15, 2021

(86) PCT No.: PCT/KR2021/003165
§ 371 (c)(1),
(2) Date: Dec. 2, 2022

(87) PCT Pub. No.: WO2022/173070
PCT Pub. Date: Aug. 18, 2022

(65) Prior Publication Data
US 2023/0190353 A1 Jun. 22, 2023

(30) Foreign Application Priority Data
Feb. 9, 2021 (KR) .................. 10-2021-0018060

(51) Int. Cl.
*A61B 17/92* (2006.01)
*A61F 2/46* (2006.01)
*A61B 17/00* (2006.01)

(52) U.S. Cl.
CPC ...... *A61B 17/92* (2013.01); *A61B 2017/0046* (2013.01); *A61B 2017/00407* (2013.01);
(Continued)

(58) Field of Classification Search
CPC ........ A61B 2017/924; A61B 2017/925; A61B 2017/927; A61B 2017/928; A61F 2002/4681; B25D 16/00; B25B 21/02
See application file for complete search history.

(56) References Cited

U.S. PATENT DOCUMENTS 3,207,237 A * 9/1965 Wanner .................. B25B 21/02
173/205
4,712,625 A * 12/1987 Kress ..................... B25D 16/00
173/104
(Continued)

FOREIGN PATENT DOCUMENTS

EP 1114700 A2 7/2001
JP S63013671 U 1/1988
(Continued)

*Primary Examiner* — David W Bates
(74) *Attorney, Agent, or Firm* — Rabin & Berdo, P.C.

(57) ABSTRACT

An impactor according to an embodiment of the present invention comprises an adapter detachably coupled to a rotary power tool, wherein the adapter includes: a case part; a tool coupling part receiving a rotational force from the rotary power tool; a first rotating part rotating in association with rotation of the tool coupling part in only one direction among rotation directions of the tool coupling part; a striking part transfer part rotating in association with rotation of the first rotating part; a striking part which is moved, while compressing a first spring, in a first direction by rotation of the striking part transfer part and then moved in a second direction opposite to the first direction by a restoring force of the first spring; and a force transfer part moved in the second direction by contact with the striking part.

12 Claims, 12 Drawing Sheets

(52) U.S. Cl.
 CPC ... *A61B 2017/925* (2013.01); *A61B 2017/928* (2013.01); *A61F 2002/4681* (2013.01)

(56) References Cited

U.S. PATENT DOCUMENTS

| | | | |
|---|---|---|---|
| 5,881,855 A * | 3/1999 | Putney | B25B 21/02 192/75 |
| 2006/0024141 A1 * | 2/2006 | Schad | B25D 16/00 408/8 |
| 2012/0152577 A1 * | 6/2012 | Mattson | B25D 17/088 81/436 |
| 2014/0338942 A1 * | 11/2014 | Putney | F16H 25/08 173/205 |
| 2015/0129268 A1 | 5/2015 | Herr | |
| 2018/0338751 A1 * | 11/2018 | Pedicini | A61F 2/4603 |
| 2019/0183555 A1 * | 6/2019 | Pedicini | B25D 17/005 |
| 2019/0216521 A1 * | 7/2019 | Chhatrala | A61F 2/4603 |

FOREIGN PATENT DOCUMENTS

| | | |
|---|---|---|
| JP | 2002127043 A | 5/2002 |
| KR | 1020090103231 A | 10/2009 |

* cited by examiner

ORTHOPEDIC IMPACTOR

TECHNICAL FIELD

The present disclosure relates to an orthopedic impactor.

BACKGROUND ART

As the aging of the population in the world intensifies, the demand for hip replacement surgery continues to increase. In addition, in recent years, the number of cases in which young patients undergo hip joint surgery due to various inflammations, tumors, and excessive exercise is also increasing.

Hip replacement surgery is an operation to replace one or both of the joints with artificial joint(s) when there is an abnormality in the joint or bone that connects the hip bone (acetabulum) and the thigh bone (femur).

Meanwhile, in this surgical procedure, the process of inserting the femoral stem into the correct position in the femur is one of the factors that determine the prognosis of the operation. In the related art, in order to insert the femoral stem into the femur, a broach is first inserted into the femur and then removed to form a space, and then the femoral stem is inserted into this space.

Meanwhile, the related art uses the method as illustrated in FIG. 12, in which a doctor manually applies blows to the broach 300 using a tool such as a mallet (M) to insert it into the femur 400 to form a space for stem insertion. However, in this case, since the magnitude and direction of the impact applied to the broach 300 are not constant, an abnormal space is formed in the femur. As a result, there is a problem in that, when the femoral stem is inserted into this space, the prognosis of the operation deteriorates, requiring reoperation.

DETAILED DESCRIPTION OF INVENTION

Technical Problem

The present disclosure has been made to overcome the problems mentioned above, and it is an object of the present disclosure to provide an orthopedic impactor capable of applying a constant impact on an object at regular intervals during orthopedic surgery.

Technical Solution

In order to achieve the objects mentioned above, an impactor according to an embodiment of the present disclosure includes an adapter detachably coupled to a rotary power tool, in which the adapter may include a case part, a tool coupling part receiving a rotational force from the rotary power tool, a first rotating part rotating in association with rotation of the tool coupling part in only one direction among rotation directions of the tool coupling part, a striking part transfer part rotating in association with the rotation of the first rotating part, a striking part which is moved, while compressing a first spring, in a first direction by the rotation of the striking part transfer part and then moved in a second direction opposite to the first direction by a restoring force of the first spring, and a force transfer part moved in the second direction by contact with the striking part.

In addition, the tool coupling part and the first rotating part may be in a ratchet coupling so as to be rotated in association with each other only in the one direction.

In addition, the striking part transfer part may include a bore with one open end, a second spring disposed inside the bore, and a first bar connected at both ends to an inner wall of the bore, in which the first rotating part may include a rectangular groove extending in a longitudinal direction, the first bar may pass through the rectangular groove, and one end of the second spring may be in contact with a bottom surface of the bore and the other end of the second spring is in contact with the first rotating part.

In addition, the striking part transfer part may include a plurality of screw thread parts, screw valley parts formed between the plurality of screw thread parts, and a longitudinal groove part extending in the longitudinal direction.

In addition, the striking part transfer part may be rotationally symmetrical by 180° with respect to a longitudinal central axis.

In addition, the striking part may include a body having a bore with one open side, and a second bar passing through a wall of the body, and including one end of which protrudes toward the bore and the other end of which protrudes toward an outside of the body, in which the second bar may include two second bars provided to face each other at 180° intervals.

In addition, when the striking part transfer part is rotated, the one end of the second bar is moved along the screw valley part, and if the one end of the second bar is moved out of the screw valley part and reaches the longitudinal groove part, the striking part is moved in the second direction by a restoring force of the first spring.

In addition, the force transfer part may include a force transfer part body, a flange part protruding from an outer surface of the force transfer part body, and a third spring disposed to surround the force transfer part body on one side based on the flange part, in which a distal end of the force transfer part body may protrude from the case part, and one end of the third spring may be in contact with an inner wall of the case part and the other end may be in contact with the flange part.

In addition, the case part may further include a locking jaw on which the flange part can be caught, and a longitudinal through-hole through which the second bar can be moved.

In addition, a first bearing may be disposed between the case part and the striking part transfer part, and a second bearing may be disposed between the case part and the tool coupling part.

In addition, one end of the first spring may be in contact with the first bearing and the other end of the first spring may be in contact with the striking part.

In addition, the case part may include a first compartment formed on a left side with respect to the locking jaw, and a second compartment formed on a right side with respect to the locking jaw, and the force transfer part may be positioned in the first compartment, and the striking part, the striking part transfer part, the first rotating part, and the tool coupling part may be arranged in the second compartment in turn.

In addition, when the striking part is moved to right side in association with the rotation of the striking part transfer part, the force transfer part may be moved to the right side by a restoring force of the third spring and the flange part may be in a state of being caught on the locking jaw of the case part, in which a portion of the force transfer part may be in a state of protruding farthest into the second compartment.

Advantageous Effects

The orthopedic impactor having the configuration described above according to an embodiment of the present disclosure has the following effects.

According to the orthopedic impactor, it is possible to apply a certain impact to the object at regular intervals during orthopedic surgery.

In addition, by controlling the number of rotations of the tool coupling part, the frequency of hitting applied to the object can be easily adjusted as desired.

In addition, since the target can be inserted into the femur by hitting the target several times with a weak force using this impactor, it is safer than related surgical methods and can significantly reduce the probability of fractures.

Meanwhile, although the present disclosure is not explicitly described, it also includes other effects that can be expected from the configuration described above.

BEST MODE FOR EMBODYING INVENTION

Hereinafter, preferred embodiments of the present disclosure will be described in detail with reference to the accompanying drawings, which will be readily apparent to those skilled in the art to which the present disclosure pertains. However, it will be understood that the present disclosure can be implemented in various other different forms and should not be construed as being limited to certain examples described herein.

Figure 1:
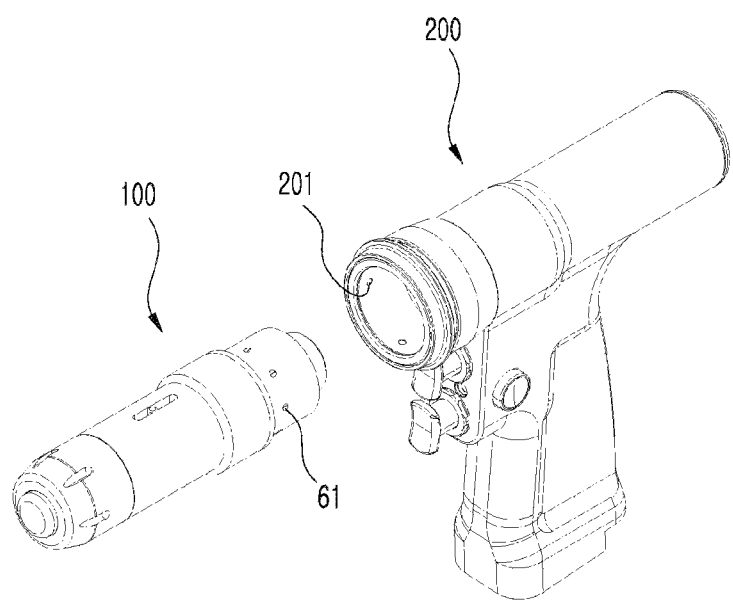
FIG. 1 is a schematic diagram of an impactor according to an embodiment of the present disclosure.

As illustrated in FIG. 1, an impactor according to an embodiment of the present disclosure includes an adapter 100 detachably coupled to a rotary power tool 200. The rotary power tool 200 may be a known power tool, and the adapter 100 may be coupled to the rotary power tool 200 with various known mechanical coupling methods. In this embodiment, by way of example, a plurality of hemispherical grooves 61 recessed at intervals in a circumferential direction may be formed on the outside of a case part 6 of the adapter to be described below, and to correspond to the hemispherical grooves 61, the rotary power tool 200 may have a plurality of protruding hemispherical protrusions 201 formed therein, so that the adapter 100 and the rotary power tool 200 can be coupled or uncoupled.

Figure 2:
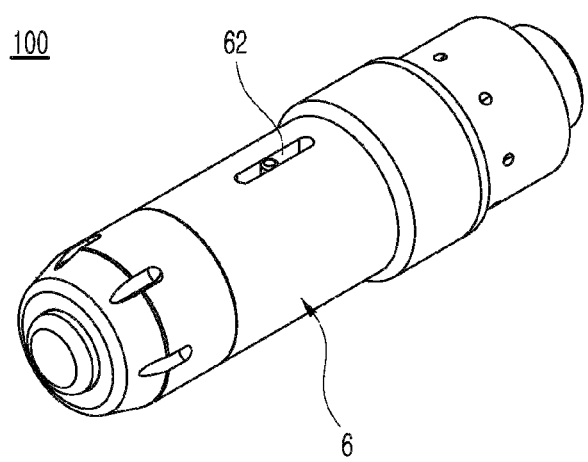
FIG. 2 shows the impactor of FIG. 1.
Figure 3:
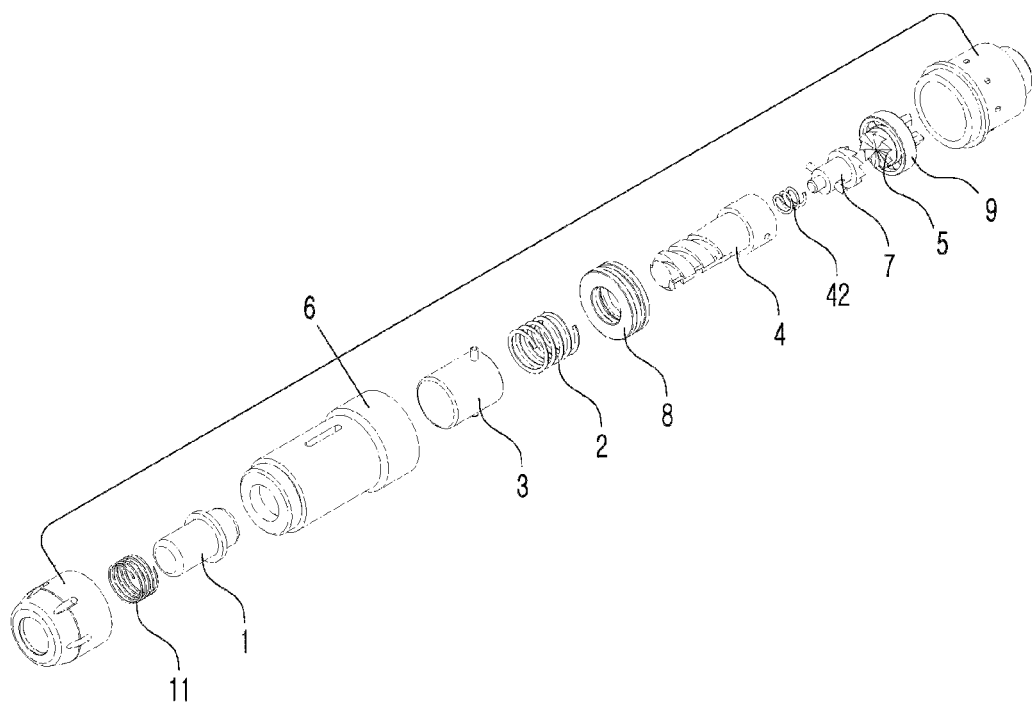
FIG. 3 is an exploded view of a main configuration of the impactor of FIG. 2.
Figure 4:
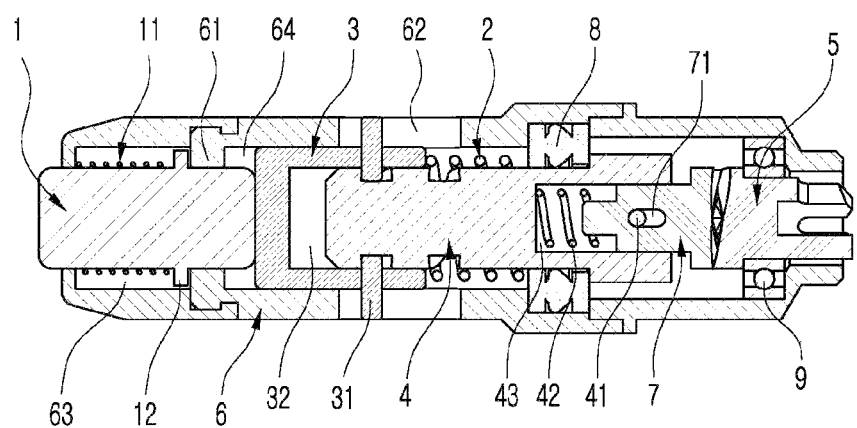
FIG. 4 is a cross-sectional view of the impactor of FIG. 2.

As illustrated in FIGS. 2 to 4, the adapter 100 includes, as main components, the case part 6, a tool coupling part 5, a first rotating part 7, a striking part transfer part 4, a striking part 3, and a force transfer part 1.

The case part 6 includes a locking jaw 61 on which a flange part 12 of the force transfer part 1 to be described below may be caught, and a longitudinal through hole 62 through which a second bar 31 of the striking part 3 to be described below can be moved. In addition, with respect to the locking jaw 61, there are a first compartment 63 formed on the left side (based on FIG. 4) and a second compartment 64 formed on the right side. The force transfer part 1 is positioned in the first compartment 63, and the striking part 3, the striking part transfer part 4, the first rotating part 7, and the tool coupling part 5 are arranged in the second compartment 64 in turn.

The tool coupling part 5 receives the rotational force of the rotary power tool to be rotated. To this end, as illustrated in FIG. 4, a second bearing 9 is disposed between the case part 6 and the tool coupling part 5.

Figure 5A:
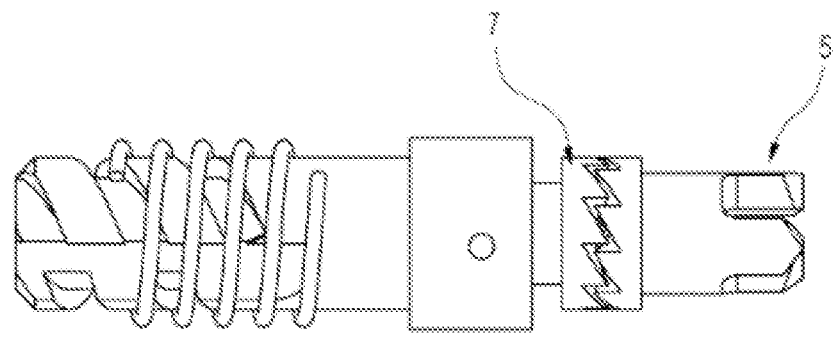
FIG. 5A and FIG. 5B are views illustrating a coupling relationship between a first rotating part and a tool coupling part of the impactor of FIG. 2.
Figure 5B:
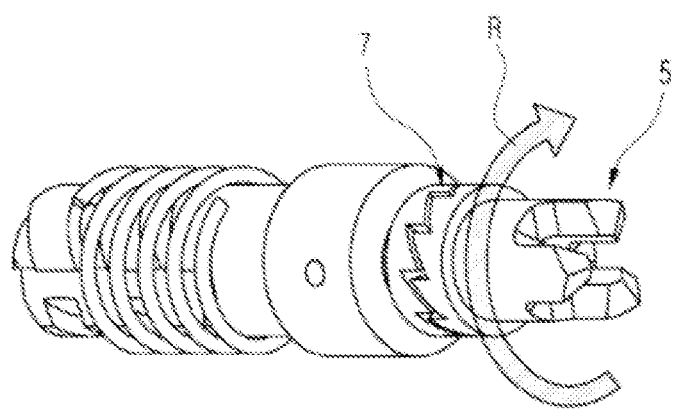

As illustrated in FIG. 5A and FIG. 5B, the first rotating part 7 is rotated in association with the rotation of the tool coupling part 5 only in one (counterclockwise direction, based on FIG. 5B) of the rotational directions of the tool coupling part 5. To this end, the tool coupling part 5 and the first rotating part 7 are ratchet coupled, so that the relative movement is limited only in one direction (R). For reference, a ratchet coupling refers to a coupling that restricts the movement of a mechanical element to only one side. Therefore, when the tool coupling part 5 is rotated in the clockwise direction (R), the first rotating part 7 is rotated in association with the rotation of the tool coupling part 5.

When the tool coupling part 5 is rotated in the opposite direction, that is, in the clockwise direction (based on FIG. 5A), the first rotating part 7 is pushed to the left (based on FIG. 5A) such that the first rotating part 7 can not be moved in association with the tool coupling part 5. In this regard, as illustrated in FIG. 6B, the first rotating part 7 includes a rectangular groove 71 extending in its longitudinal direction.

The striking part transfer part 4 is rotated in association with the rotation of the first rotating part 7. To this end, as illustrated in FIG. 4, a first bearing 8 is disposed between the case part 6 and the striking part transfer part 4.

Figure 6A:
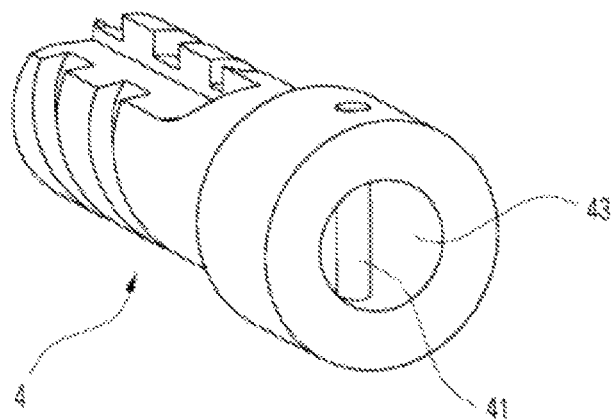
FIG. 6A and FIG. 6B illustrate a coupling relationship of the first rotating part and a striking part transfer part of the impactor of FIG. 2.
Figure 6B:
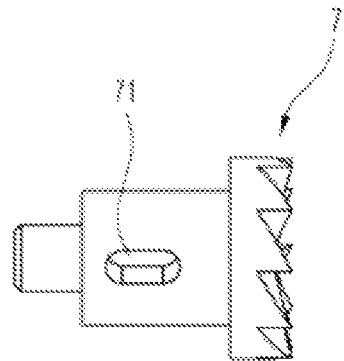

As illustrated in FIGS. 4 and 6A, the striking part transfer part 4 includes a bore 43 into which a distal end of the first rotating part 7 is inserted, a second spring 42 disposed inside the bore 43, and a first bar 41 connected at both ends to the inner wall of the bore 43. In this case, the first bar 41 passes through the rectangular groove 71 of the first rotating part 7, and one end of the second spring 42 is in contact with the bottom surface of the bore 43 and the other end is in contact with the first rotating part 7. Through this, by the restoring force of the second spring 42, the first rotating part 7 is constantly subjected to a force toward the direction of the tool coupling part 5. In addition, as described above, based on FIG. 5B, when the tool coupling part 5 is rotated in the counterclockwise direction, the first rotating part 7 is moved to the left (based on FIG. 4) relative to the tool coupling part 5 so as not to be moved in association with the tool coupling part 5. For reference, at this time, the first bar 41 is moved within a longitudinal groove 71 relatively to the right side.

Figure 7A:
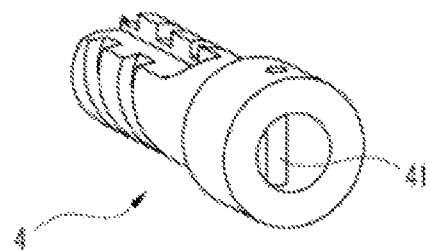
FIG. 7A, FIG. 7B and FIG. 7C are perspective views of the striking part transfer part of the impactor of FIG. 2 viewed from various directions.
Figure 7B:
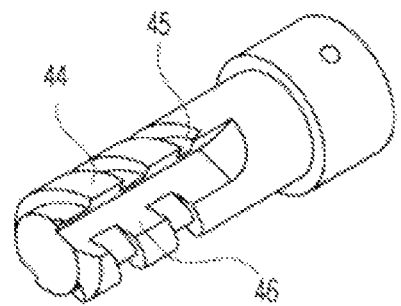
Figure 7C:
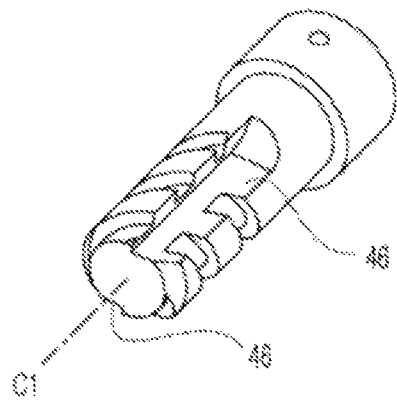

In addition, as illustrated in FIG. 7A, FIG. 7B and FIG. 7C, the striking part transfer part 4 includes a plurality of screw thread parts 44, screw valley part 45 formed between the plurality of screw thread parts 44, and a longitudinal groove part 46 extending in the longitudinal direction. In this example, the striking part transfer part 4 may be 180° rotationally symmetric with respect to a longitudinal central axis C1 (see FIG. 7C).

Figure 8:
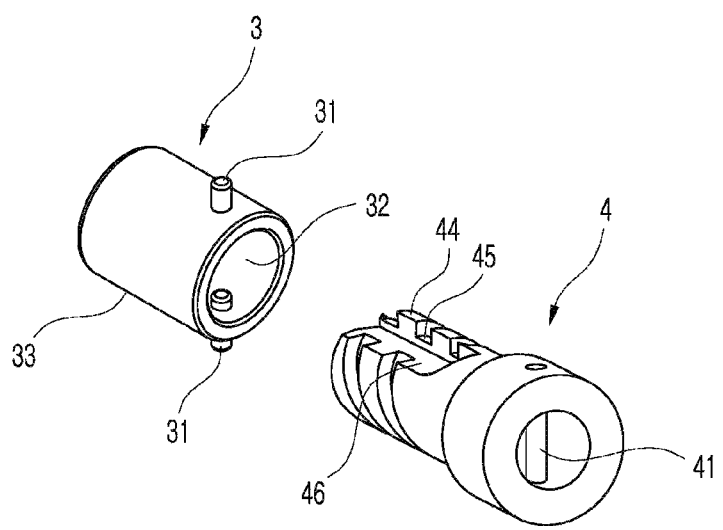
FIG. 8 illustrates a coupling relationship between the striking part and the striking part transfer part of the impactor of FIG. 2.

Referring to FIGS. 4 and 8, by the rotation of the striking part transfer part 4, the striking part 3 is moved in a first direction (to the right direction based on FIG. 4) while compressing a first spring 2, and then, by the restoring force of the first spring 2, moved in a second direction (to the left direction based on FIG. 4) opposite to the first direction. For reference, one end of the first spring 2 is in contact with the first bearing 8, and the other end is in contact with the striking part 3.

Specifically, the striking part 3 includes a body 33 including a bore 32 with one open side, and the second bar 31 with one end protruding toward the bore 32 through a wall of the body 33 in the transverse direction of the body 33, and the other end protruding to the outside of the body 33. There may be two second bars 31 provided so as to face each other at intervals of 180°.

Figure 10A:
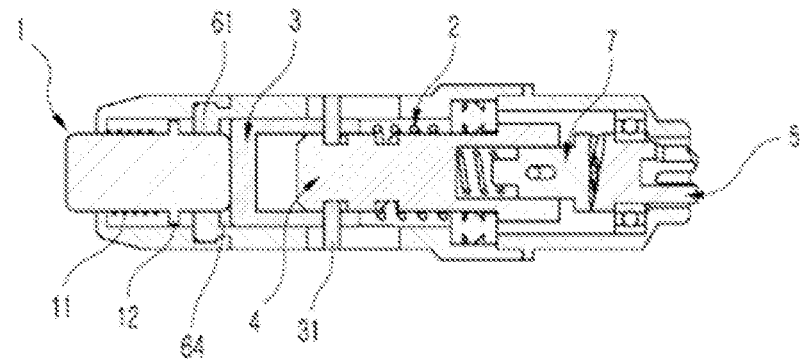
FIG. 10A, FIG. 10B and FIG. 10C are views illustrating the operation of the impactor of FIG. 2.

When the striking part transfer part 4 is rotated, the second bar 31 of the striking part 3 is moved along the screw valley part 45 of the striking part transfer part 4 (at this time, as shown in FIG. 10A, the second bar 31 comes in contact with a left wall of the screw valley part 45), and when the second bar 31 comes out of the screw valley part 45 and reaches the longitudinal groove part 46, the striking part 3 is rapidly moved in the second direction (to the left direction based on FIG. 4) by the restoring force of the first spring 2.

The force transfer part 1 is moved in the second direction (to left direction based on FIG. 4) by contact with the rapidly moved striking part 3.

Figure 9:
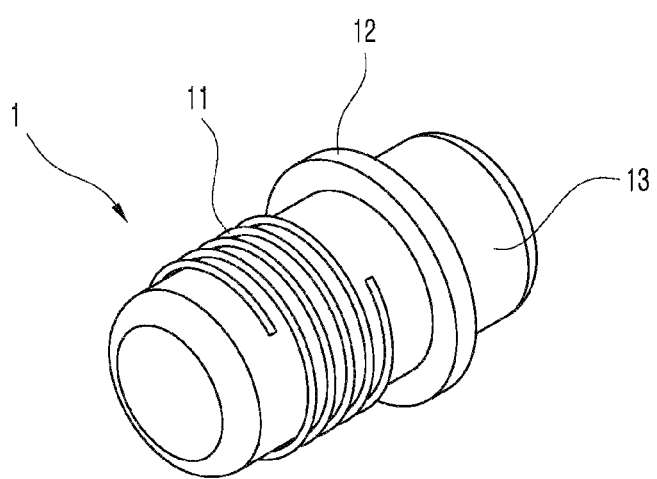
FIG. 9 is a perspective view of a main configuration of a force transfer part of the impactor of FIG. 2.

Referring to FIGS. 4 and 9, the force transfer part 1 includes a force transfer part body 13, the ring type flange part 12 protruding from an outer surface of the force transfer part body 13, and a third spring 11 disposed to surround the force transfer body part 13 on one side (left side based on FIG. 4) with respect to the flange part 12.

The distal end of the force transfer part body 13 protrudes from the case part 6.

The third spring 11 is in a compressed state, with its one end in contact with the inner wall of the case part 6 and the other end in contact with the flange part 12. Therefore, when no other load is applied to the force transfer part body 13 from the outside, the flange part 12 of the force transfer body 13 is maintained in contact with the locking jaw 61 of the case part 6 by the restoring force of the third spring 11.

Figure 10B:
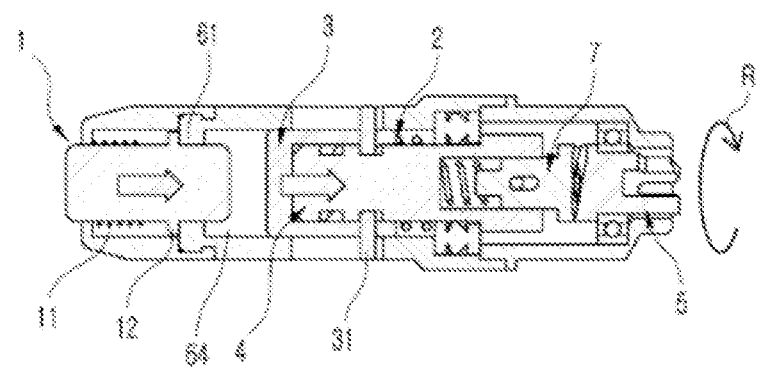
Figure 10C:
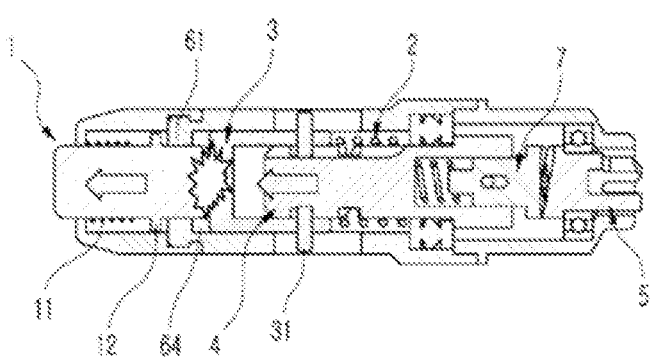

Hereinafter, the operation of the impactor having the configuration as described above according to an embodiment of the present disclosure will be described. FIG. 10A, FIG. 10B and FIG. 10C illustrate the adapter 100 of the present disclosure in the state of being coupled to the rotary power tool, and the rotary power tool is not illustrated for convenience of explanation.

FIG. 10A illustrates a state in which the rotational force of the rotary power tool is not transferred to the tool coupling part 5, that is, a non-operational state of the rotary power tool. At this time, by the restoring force of the first spring 2, the striking part 3 is in contact with the force transfer part 1. In addition, one end of the second bar 31 of the striking part 3 is positioned in the screw valley part 45 of the striking part transfer part 4 (see FIG. 11A).

Next, as illustrated in FIG. 10B, when the rotational force in the clockwise direction (R) is applied to the tool coupling part 5, by the first rotating part 7, the striking part transfer part 4 is also rotated in association with the rotation of the tool coupling part 5. In addition, as the striking part transfer part 4 is rotated, the second bar 31 of the striking part 3 is moved along the screw valley part 45 of the striking part transfer part 4. As the striking part 3 is moved gradually to the right side, more and more elastic energy is accumulated in the first spring 2 (see FIG. 11B).

At this time, the force transfer part 1 is moved to the right side by the restoring force of the third spring 11 so that the flange part 12 is caught on the locking jaw 61 of the case part 6, and the left end of the force transfer part 1 is in the state of protruding farthest into the second compartment 64 of the case part 6.

Next, as illustrated in FIG. 10C, when the second bar 31 of the striking part 3 is moved out of the screw valley part 45 of the striking part transfer part 4 and reaches the longitudinal groove part 46, by the restoring force of the first spring 2, the striking part 3 is rapidly moved in the second direction (to the left direction based on FIG. 10A, FIG. 10B and FIG. 10C).

Figure 11A:
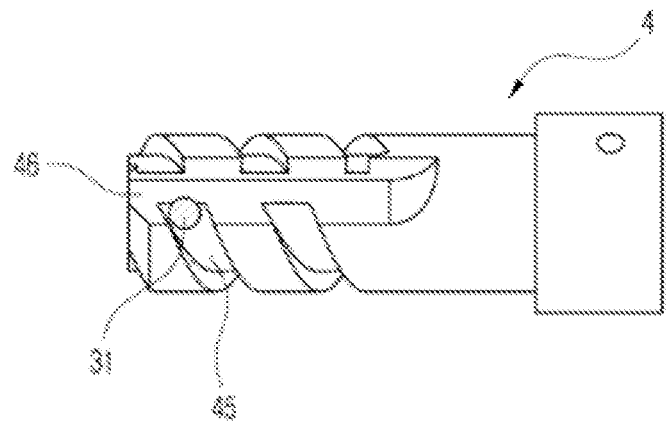
FIG. 11A, FIG. 11B and FIG. 11C are views illustrating a relative position of a second bar with respect to the striking part transfer part in steps A to C of FIG. 10A, FIG. 10B and FIG. 10C, respectively.
Figure 11B:
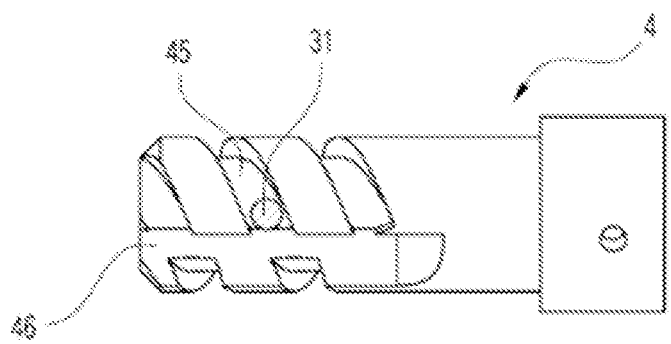
Figure 11C:
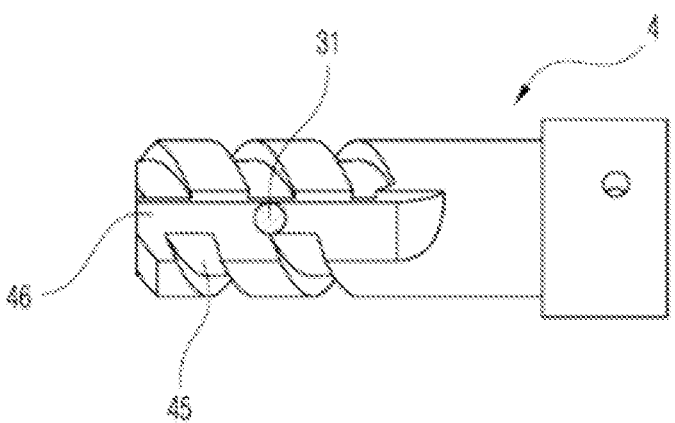
Figure 12:
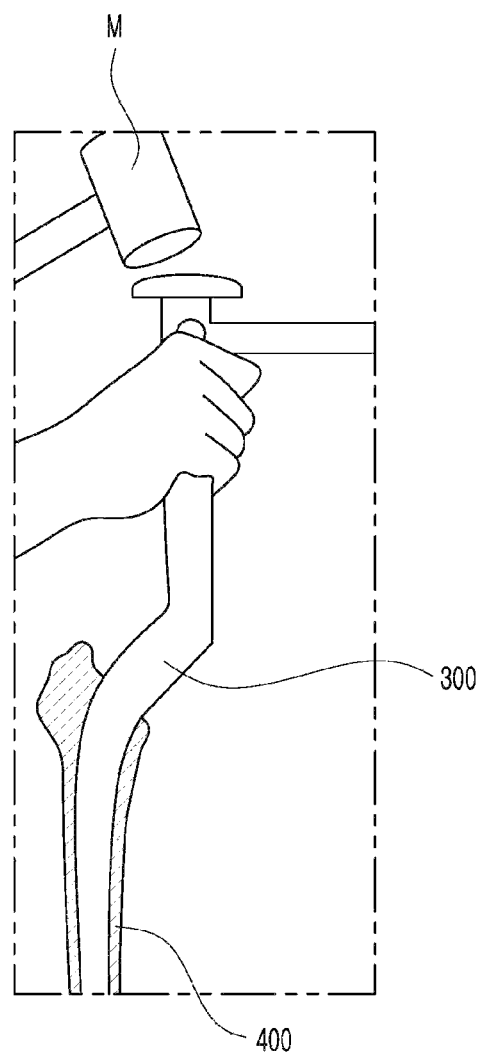
FIG. 12 illustrates a related method of manually applying a blow to an object using a mallet (M) to insert it into the femur.

Finally, when the striking part 3 strongly strikes the force transfer part 1, the force transfer part 1 transfers the striking force of the striking part 3 to the object while overcoming the restoring force of the third spring 11. For reference, FIGS. 11A to 11C are views corresponding to FIGS. 10A to 10C, respectively, schematically showing the relative position of the second bar 31 in the striking part transfer part 4 in each step.

In this example, when the striking part 3 is further rotated, the second bar 31 of the striking part 3 re-enters the screw valley part 45 of the striking part transfer part 4, and the process as described above is repeated.

Although the present disclosure has been described in connection with some examples herein, the present disclosure should not be limited to those examples only, and various other changes and modifications made by those skilled in the art from the basic concept of the disclosure are also within the scope of the claims appended herein.

INDUSTRIAL APPLICABILITY

The present disclosure can be used in orthopedic procedures such as hip replacement surgery and the like.

The invention claimed is:

1. An impactor comprising an adapter detachably coupled to a rotary power tool, wherein the adapter comprises:
   a case part;
   a tool coupling part receiving a rotational force from the rotary power tool;
   a first rotating part rotating in association with rotation of the tool coupling part in only one direction among rotation directions of the tool coupling part;
   a striking part transfer part rotating in association with the rotation of the first rotating part;
   a striking part which is moved, while compressing a first spring, in a first direction by the rotation of the striking part transfer part and then moved in a second direction opposite to the first direction by a restoring force of the first spring; and
   a force transfer part moved in the second direction by contact with the striking part, wherein the striking part transfer part includes a bore with one open end, a second spring disposed inside the bore, and a first bar connected at both ends to an inner wall of the bore, the first rotating part includes a rectangular groove extending in a longitudinal direction, the first bar passes through the rectangular groove, and one end of the second spring is in contact with a bottom surface of the bore and the other end of the second spring is in contact with the first rotating part.

2. The impactor according to claim 1, wherein the tool coupling part and the first rotating part are in a ratchet coupling so as to be rotated in association with each other in said only one direction.

3. The impactor according to claim 1, wherein the striking part transfer part includes a plurality of screw thread parts, screw valley parts formed between the plurality of screw thread parts, and a longitudinal groove part extending in the longitudinal direction.

4. The impactor according to claim 3, wherein the striking part transfer part is rotationally symmetrical by 180° with respect to a longitudinal central axis.

5. The impactor according to claim 4, wherein the striking part includes:

a body having a bore with one open side; and a second bar passing through a wall of the body, and including one end of which protrudes toward the bore and the other end of which protrudes toward an outside of the body, wherein the second bar includes two second bars provided to face each other at 180° intervals.

6. The impactor according to claim 5, wherein, when the striking part transfer part is rotated, the one end of the second bar is moved along the screw valley part, and if the one end of the second bar is moved out of the screw valley part and reaches the longitudinal groove part, the striking part is moved in the second direction by a restoring force of the first spring.

7. The impactor according to claim 1, wherein the force transfer part includes:

a force transfer part body;

a flange part protruding from an outer surface of the force transfer part body; and a third spring disposed to surround the force transfer part body on one side based on the flange part, wherein a distal end of the force transfer part body protrudes from the case part, and one end of the third spring is in contact with an inner wall of the case part and the other end is in contact with the flange part.

8. The impactor according to claim 7, wherein the case part further includes:

a locking jaw on which the flange part can be caught; and a longitudinal through-hole through which a second bar can be moved.

9. The impactor according to claim 1, wherein a first bearing is disposed between the case part and the striking part transfer part, and a second bearing is disposed between the case part and the tool coupling part.

10. The impactor according to claim 9, wherein one end of the first spring is in contact with the first bearing and the other end of the first spring is in contact with the striking part.

11. The impactor according to claim 8, wherein the case part includes a first compartment formed on a left side with respect to the locking jaw, and a second compartment formed on a right side with respect to the locking jaw, and the force transfer part is positioned in the first compartment, and the striking part, the striking part transfer part, the first rotating part, and the tool coupling part are arranged in the second compartment in turn.

12. The impactor according to claim 11, wherein, when the striking part is moved to right side in association with the rotation of the striking part transfer part, the force transfer part is moved to the right side by a restoring force of the third spring and the flange part is in a state of being caught on the locking jaw of the case part, wherein a portion of the force transfer part is in a state of protruding farthest into the second compartment.

* * * * *